(12) United States Patent
Shakespeare et al.

(10) Patent No.: US 6,343,240 B1
(45) Date of Patent: Jan. 29, 2002

(54) METHOD FOR IDENTIFYING PLURAL RELATIONS IN A SHEET MANUFACTURING PROCESS

(75) Inventors: John Shakespeare, Siuro; Tapio Metsälä, Tampere, both of (FI)

(73) Assignee: Neles Paper Automation OY, Tampere (FI)

( * ) Notice: Subject to any disclaimer, the term of this patent is extended or adjusted under 35 U.S.C. 154(b) by 0 days.

(21) Appl. No.: 09/141,434

(22) Filed: Aug. 27, 1998

Related U.S. Application Data

(60) Provisional application No. 60/068,926, filed on Dec. 29, 1997.

(51) Int. Cl.[7] .................................................. G06F 7/66
(52) U.S. Cl. ........................ 700/129; 700/128; 700/127; 700/122; 162/100; 73/159; 264/167; 264/171.22
(58) Field of Search ............................. 700/129, 38, 53, 700/122, 127, 128; 702/167, 189; 162/198, 100; 73/159; 264/167, 171.22

(56) References Cited

U.S. PATENT DOCUMENTS

| | | | | |
|---|---|---|---|---|
| 3,936,665 A | * | 2/1976 | Donoghue | 700/129 |
| 4,633,420 A | * | 12/1986 | Masanobu | 702/167 |
| 4,874,467 A | * | 10/1989 | Karlsson | 162/198 |
| 4,903,528 A | * | 2/1990 | Balakrishnan | 73/159 |
| 4,947,684 A | * | 8/1990 | Balakrishnan | 73/159 |
| 4,965,736 A | * | 10/1990 | Balakrishnan | 700/129 |
| 5,229,140 A | * | 7/1993 | Crass | 425/141 |
| 5,400,247 A | * | 3/1995 | He | 700/53 |
| 5,400,258 A | * | 3/1995 | He | 700/129 |
| 5,539,634 A | | 7/1996 | He | 364/158 |
| 5,658,432 A | * | 8/1997 | Heaven | 206/554 |
| 5,685,955 A | * | 11/1997 | Leigraf | 162/198 |
| 5,893,055 A | * | 4/1999 | Chen | 702/189 |

* cited by examiner

Primary Examiner—William Grant
Assistant Examiner—Ronald D Hartman, Jr.
(74) Attorney, Agent, or Firm—Ladas & Parry

(57) ABSTRACT

The invention relates to method for identifying plural relations in a sheet manufacturing process. Sheet properties are deduced from a response in a pseudo-property profile to a cyclic stimulation. A pseudo-property profile is calculated using a phase lag equal to half the stimulation cycle time, with and without stimulation. The properties of the sheet are deduced from the difference between an excited pseudo-property profile and a reference pseudo-property profile.

13 Claims, 2 Drawing Sheets

METHOD FOR IDENTIFYING PLURAL RELATIONS IN A SHEET MANUFACTURING PROCESS

This application claims the benefit of U.S. Provisional Application No. 60/068,926 filed Dec. 29, 1997.

FIELD OF THE INVENTION

The invention relates to a method for identifying plural relations in a continuous sheet manufacturing process.

BACKGROUND OF THE INVENTION

Plural actuators are commonly deployed across a sheet making apparatus in order to regulate one or more properties of the sheet in the cross machine direction. Sheet properties are commonly measured at a plurality of locations across the sheet, where such plurality of measurement locations across the sheet normally equals or exceeds the plurality of actuators. The effect of an actuator on a measured sheet property is referred to as the response of the actuator. The set of locations of the centres of responses for each actuator is referred to as the mapping for the actuators. Efficacy of the regulation of sheet properties in the cross machine direction by governing such actuators is determined for example by the accuracy of the mapping and response information employed by regulation means.

U.S. Pat. No. 5,400,258 discloses a method in which prior knowledge of the response shape is used in a pattern matching scheme for estimating mapping positions from the change to a measured profile caused by a bump test. In U.S. Pat. No. 5,539,634, the mapping is deduced from the effect on the apparent noise profile of a sheet property caused by cycling one or more actuators. In the above cases bump tests cause marks in the sheet. Further the prior art in this field requires that a method of identifying responses or mapping has exclusive governance over the actuators during the period of identification, e.g. it is required that no other excitation of the actuators occur during the excitation for purposes of identification.

Accordingly, it is an object of the present invention to provide an improved method for identifying sheet property relationships in a continuous sheet manufacturing process.

SUMMARY OF THE INVENTION

Preferably the present method comprises the steps of a) specifying a first time period to be used as the cycle time of a cyclic excitation, b) measuring a sheet property profile, c) calculating a reference pseudo-property profile from plural measurements of said measured sheet property profiles using a phase lag substantially equal to half of said first time period, d) applying a cyclic excitation pulse to at least one actuator, with a cycle time substantially equal to the first time period, e) measuring an excited sheet property profile, f) calculating an excited pseudo-property profile from plural measurements of the measured excited sheet profiles using a phase lag substantially equal to half of said first time period, and g) deducing properties of the sheet from the difference between said excited pseudo-property profile and said reference pseudo-property profile.

BRIEF DESCRIPTION OF THE DRAWINGS

The invention will be described in greater detail in conjunction with the attached drawings, in which.

DETAILED DESCRIPTION OF PREFERRED EMBODIMENTS

The basic idea of the invention is that a cyclic excitation is used. Properties of the sheet manufacturing process are deduced from the response in a pseudo-property profile to the stimulation. The pseudo-property profile is calculated using a phase lag equal to half the excitation cycle time, with and without stimulation. The pseudo-property profile can be the correlated variability or correlated difference in a measured profile of a sheet property, where the correlation is performed with a lag substantially equal to half the excitation cycle time.

An advantage of the invention is that smaller excitation amplitudes can be used than with prior art methods, hence introducing less disturbances to the process. A further advantage is that the actuators may be governed by sheet property regulating means during the identification tests, without reducing the efficacy of the identification.

Figure 1:
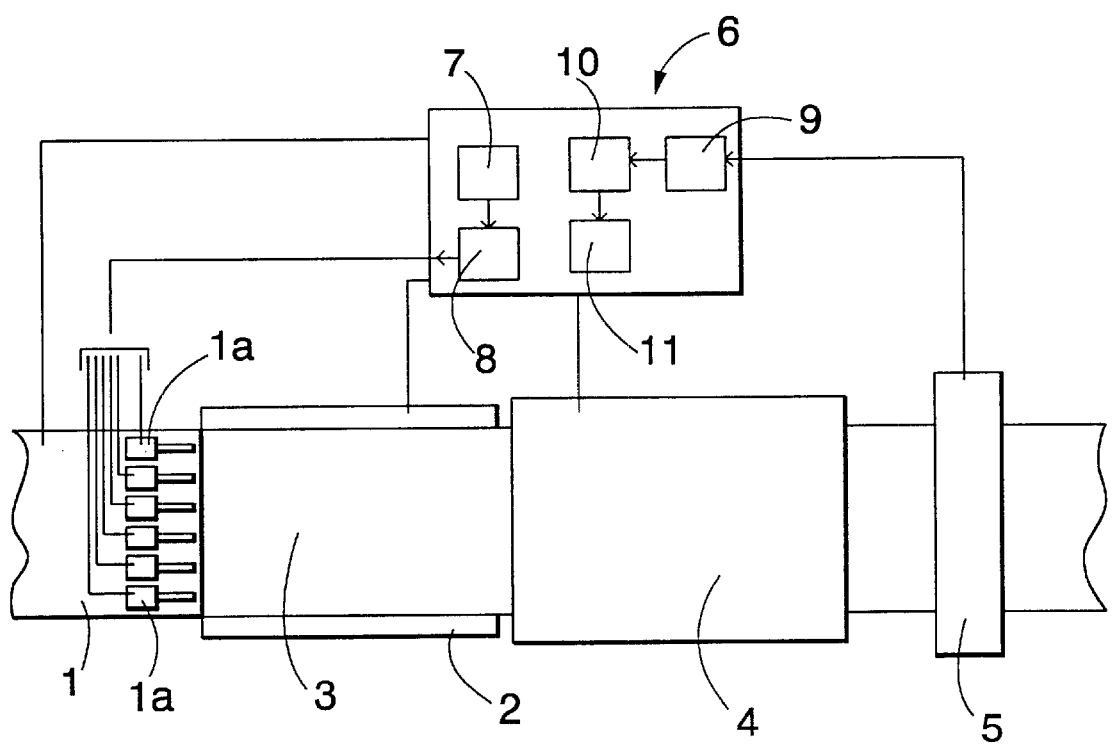
FIG. 1 is a schematic top view of a part of a paper or board machine, and FIG. 2 schematically shows an excitation pulse and its response in accordance with the present method.

FIG. 1 is a schematic top view of a part of a paper or board machine. Paper and paper board and tissue manufacturing processes are examples of continuous sheet making processes. A paper machine comprises a headbox 1, from which pulp is fed into a former 2 in which a fiber web 3 is formed of the pulp. The headbox 1 comprises e.g. actuators 1*a* for adjusting the position of the slice lip at respective points so as to affect the cross-directional properties of the fiber web 3. A small portion of the web 3 is commonly trimmed off at each edge of the web 3, between the headbox 1 and the drying section 4. The fiber web 3 is dried in a drying section 4 after which a measuring frame 5 is arranged for measuring the machine-direction and cross-directional properties of the fiber web 3 in a manner known per se. A paper machine further comprises e.g. a press section and a reel, and possibly also e.g. size presses or a calender, not shown in FIG. 1 for the sake of clarity. Furthermore, the operation of a paper machine is fully known per se to those skilled in the art and is therefore not described in any more detail here.

The equipment further comprises a control unit 6 for assembling data concerning the fiber web 3 and the adjustments and operating statuses of the different parts of the paper machine. On the basis of the assembled data, the control unit 6 controls the different parts and actuators of the paper machine, such as the actuators 1*a* for adjusting the slice of the headbox 1.

The control unit 6 comprises, for example, a stimulus generator 7. The stimulus generator 7 produces the required deterministic stimulus for the system, e.g. a cyclic excitation pulse. The cross-directional positions, pattern model and amount of pulses are freely selectable. The excitation pulse from the stimulus generator 7 is fed into a dual master cross-directional actuator handler 8. The aforesaid actuator handler 8 controls for example the actuators 1*a* for adjusting respective portions of the slice of the headbox 1. Information for controlling the sheet properties is also fed to actuator handler 8, and if the information is fed simultaneously with the pulses from the stimulus generator 7, the information will be added together in the actuator handler 8. The combined changes are then fed to the respective actuators 1*a* that control the slice.

The measured properties from the measuring frame 5 are processed in a signal processing unit 9. The signal processing unit 9 includes means for filtering the raw profile in the cross-direction and machine direction. The observer module 10 calculates the pseudo-property profile that is correlated difference or correlated variability. Result profile calculus module 11 subtracts the reference pseudo-property profile from the excited pseudo-property profile and produces the final result. The equipment and the distribution of operations performed in the equipment may differ from that shown in FIG. 1.

The process relations of interest include especially the location, magnitude and distribution of effects in a measured property of the sheet caused by changes made to an actuator.

In this invention, a first time period T1 is chosen as the cycle time for a cyclic excitation of the actuators. A first set of sheet property profiles is measured without the cyclic excitation over a second time period T2 which exceeds the first time period T1. A reference pseudo-property profile is calculated from the first set of measured sheet property profiles using a phase lag substantially equal to half of the first time period T1. A cyclic excitation with cycle time substantially equal to the first time period T1 is then applied to one or more selected actuators for a third time period T3 which exceeds the first time period T1. After a first delay D1 from the commencement of the cyclic excitation, a second set of sheet property profiles is measured over a fourth time period T4 which exceeds the first time period T1. This fourth time period T4 may continue for a second delay D2 after the cessation of the cyclic excitation. An excited pseudo-property profile is calculated from the second set of measured sheet property profiles using a phase lag substantially equal to half of the first time period T1. Properties of the sheet manufacturing processes can be deduced from the difference between the excited pseudo-property profile and the reference pseudo-property profile.

The fourth time period T4 (during which excited sheet property profiles are measured) need not coincide exactly with the third time period T3 (during which the actuators are stimulated with cyclic excitation). The first delay D1 between the commencement of the third time period T3 and the commencement of the fourth time period T4 is preferably not less than one process dead time plus one profile measurement time. The second delay D2 between the end of the third time period T3 and the end of the fourth time period T4 is preferably not greater than the sum of process dead time, profile measurement time, and the first time period T1. The first time period T1 (being the cycle time of the cyclic excitation) is preferably not less than four times the measurement time of a single profile.

The sheet property profiles are preferably first measured singly, and thereafter collected to a set, from which the pseudo-property profile may be accumulated. Alternatively, the pseudo-property profile may be accumulated incrementally as each measured sheet property profile is measured.

The pseudo-property profile is preferably the correlated variability profile or correlated difference profile calculated from the measured sheet property profiles with a phase lag substantially equal to half of the first time period T1. Definitions of the correlated variability and correlated difference profiles are given below, and a pseudo-property profile is preferably calculated in accordance with those definitions. The phase lag used in calculating pseudo-property profiles need not be equal to exactly half of the first time period T1, but may vary from that value according to the definitions of correlated variability and correlated difference given below.

The mapping locations are obtained for example from the peaks of the difference between the excited correlated variability profile and the reference correlated variability profile.

The response shapes and amplitudes are obtained for example from the difference between the excited correlated difference profile and the reference correlated difference profile.

Optionally, filtering or other denoising techniques can be applied to the measured property profiles or during calculation of the pseudo-property profiles, or during calculation of the difference between the excited pseudo-property profile and the reference pseudo-property profile.

Optionally, estimation of mapping or responses can be enhanced by pattern recognition or other signal processing techniques. For example, if the profile response is approximately known, then the expected response in the correlated variability can be calculated. Hence, the estimation of mapping can be enhanced by convoluting the change in the correlated variability profile with this expected response in correlated variability. Similarly, if the mapping is approximately known, then the locations of responses in the correlated difference profile can be calculated. Hence, the estimation of response shapes and amplitudes can be enhanced by operations such as symmetrization of segments of the change in the correlated difference profile. When reference and excited profiles are calculated for both correlated difference and correlated variability, these enhancement methods lead to recursive estimation alternately of mapping and responses, with increasing accuracy.

Figure 2:
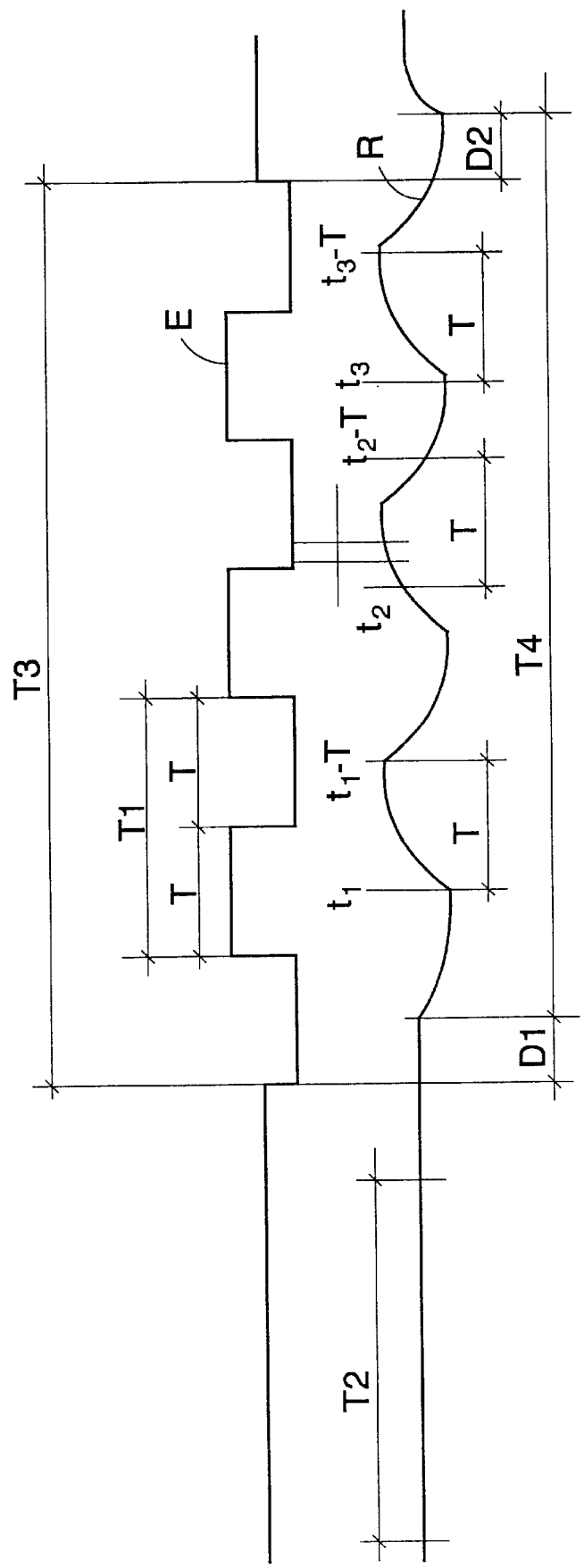

FIG. 2 illustrates a cyclic excitation pulse E and the response R caused by it in the properties to be measured from the sheet.

If the first time period T1 (being the cycle time of the cyclic excitation) is 2T, the correlated variability with phase lag T for a sheet property profile P is calculated at a measurement location $x_j$ as:

$$V(x_j, t_k) = |P(x_j, t_k - T)|^q \tag{1}$$

where q is preferably 2, but may be any integer or non-integer quantity not less than unity, and $t_k$ is the time at which that measurement was performed. In the case that $t_k - T$ does not correspond to the time of an actual measurement, the phase lagged measurement $P(X_j, t_k - T)$ may be estimated by interpolation from available measurements at $x_j$, or replaced with that measurement at $x_j$ which is closest in time to the desired phase lag T or replaced by an average of measurements at $x_j$ which are the closest several in time to the desired phase lag T.

In the simplest case, the correlated variability is accumulated by averaging over the whole accumulation time. For example, if there are M profile measurements in the accumulation time, an unweighted arithmetic average U for the correlated variability is:

$$U(x_j) = \frac{1}{M} \sum_{k=1}^{M} V(x_j, t_k) \tag{2}$$

A more sophisticated accumulation can employ other averaging techniques which need not use all of the correlated-variability profiles, or which employ weighting factors for individual correlated variability profiles, or which employ profiles of weighting factors. An improved estimate during the fourth time period T4 (during which the excited correlated variability profile is accumulated) may be derived from knowledge of the process delay, by eliminating from the accumulation any variability profiles which correspond to the state changes in the actuators, or by weighting variability profiles in the accumulation according to the expected phase of the excitation. For example:

$$U(x_j) = \frac{\sum_{k=1}^{M} w_k V(x_j, t_k)}{\sum_{k=1}^{M} w_k} \quad (3)$$

where weighting factor $w_k$ depends on the phase of $t_k$ with respect to actuator movement times $\theta_i$. The actuator movement time $\theta_i$ is the time at which the actuator/actuators was/were moved e.g. the time of stimulus i closest to $t_k$–D, where D is process delay e.g. process dead time. For example, $w_k$ is zero when $t_k$–$\theta_i$–D modulo T is near zero or is near T, and $w_k$ is unity when $t_k$–$\theta_i$–D modulo T is between T/4 and 3T/4. This method of calculating weighting factors is illustrative, rather than restrictive. The weighting factors may for example differ in cross direction as well as in time.

If the profile response R(x) is known, then the variability response S(x) can be calculated according to the definition of variability employed above:

$$S(x) = |R(x)|^q \quad (4)$$

If the first time period T1 (being the cycle time of the cyclic excitation) is 2T, the correlated difference C with phase lag T for a sheet property profile P is calculated at a measurement location $x_j$ as:

$$C(x_j, t_k) = P(x_j, t_k) - P(x_j, t_k - T) \quad (5)$$

where $t_k$ is the time at which that measurement was performed. In the case that $t_k$–T does not correspond to the time of an actual measurement, the phase lagged measurement $P(x_j, t_k-T)$ may be estimated by interpolation from available measurements at $x_j$ or replaced with that measurement at $x_j$ which is closest in time to the desired phase lag T or replaced by an average of measurements at $x_j$ which are the closest several in time to the desired phase lag T.

The correlated difference is preferably accumulated using knowledge of the approximate process delay D from the actuators to the measurement system. An estimate of the average correlated difference profile B during the fourth time period T4 (during which the excited correlated variability profile is accumulated) is derived by weighting correlated difference profiles in the accumulation according to the expected phase of the excitation. Profiles of weighting factors which need not all be equal may also be used, but the method is illustrated here for scalar factors. For example:

$$B(x_j) = \frac{\sum_{k=1}^{M} f_k C(x_j, t_k)}{\sum_{k=1}^{M} |f_k|} \quad (6)$$

where weighting factor $f_k$ depends on the phase of $t_k$ with respect to actuator movement times $\theta_j$. For example, $f_k$ is zero when $t_k$–$\theta_i$–D modulo T is near zero or is near T, and $f_k$ is of unity magnitude when $t_k$–$\theta_i$–D modulo T is between T/4 and 3T/4. The factor $f_k$ changes sign with period 2T. This method of calculating weighting factors is illustrative, rather than restrictive. The weighting factors may for example differ in cross direction as well as in time.

If plural actuators are employed, the excitation amplitudes need not be identical in magnitude or direction. Preferably, the sum of excitation magnitudes for plural actuators is small or zero. If the actuators are simultaneously governed by sheet property regulating means, the cycle time of the cyclic excitation should exceed the cycle time of the sheet property regulating means.

The first delay D1 (from commencement of the cyclic excitation to commencement of collection of the second set of sheet property profiles) is preferably approximately the same as the effective process delay from the actuators to the sheet property profile measurement (i.e. the sum of process dead time and profile measurement time). The second delay D2 (from cessation of the cyclic excitation to cessation of collection of the second set of sheet property profiles) is preferably substantially the same as the first delay D1, or longer than the first delay D1 by the length of the cycle time of the cyclic excitation. However, these delays may be shorter or longer, or may be zero, provided the third time period T3 during which the cyclic excitation takes place is several times greater than the effective process delay.

The second time period T2 (during which the reference pseudo-property profile is accumulated) need not be the same as the fourth time period T4 (during which the excited pseudo-property profile is accumulated). However, both these time periods should exceed the cycle time of the cyclic excitation, and preferably they are of similar duration.

The first time over which correlated variability profiles are accumulated (without periodic actuator excitation) need not be the same as the second accumulation time (when the excitation is active). However, both these times should exceed the period of excitation, and it is preferable that the two times are similar in duration.

The method of accumulation may use arithmetic, geometric, exponential, sliding window, or other averaging. Weight factors may be employed in the averaging, and such weight factors may be fixed, or may be calculated from the process delay and actuator movement times.

Paper machines may be equipped with a variety of cross machine actuators, situated at different places in the process. For example, a headbox may have dilution valves additionally or alternatively to slice lip actuators. Also, sectional steam boxes may be situated in the forming unit or presses, and the drying units may contain sectional infra-red heaters, water sprays, and the like. The invention may be applied to these and other cross machine actuators in a similar manner to its application to slice lip actuators.

The disclosures of the following U.S. patents are incorporated herein by reference to the extent necessary or desirable to explain the invention; He, U.S. Pat. No. 5,539,634 granted Jul. 23, 1996; and He, U.S. Pat. No. 5,400,258 granted Mar. 21, 1995.

Variations, combinations and permutations of the above as would occur to those of ordinary skill in the art are included in the scope and spirit of the invention.

What is claimed is:

1. A method for identifying plural relations in a sheet manufacturing process, the method comprising the steps of
   a) specifying a first time period to be used as the cycle time of a cyclic excitation
   b) measuring a sheet property profile,
   c) calculating a reference pseudo-property profile from plural measurements of said measured sheet property profiles using a phase lag substantially equal to half of said first time period, d) applying a cyclic excitation pulse to at least one actuator, with a cycle time substantially equal to said first time period, e) measuring an excited sheet property profile, f) calculating an excited pseudo-property profile from plural measurements of the measured excited sheet profiles using a phase lag substantially equal to half of said first time period, and g) deducing properties of the sheet manufacturing process from the difference between said excited pseudo-property profile and said reference pseudo-property profile.

2. A method as claimed in claim 1, wherein said reference pseudo-property profile is accumulated for a second time period exceeding said first time period.

3. A method as claimed in claim 1, wherein the cyclic excitation is continuing for a third time period exceeding said first time period.

4. A method as claimed in claim 2, wherein accumulation of said reference pseudo-property profile employs weighting factors which are not all equal.

5. A method as claimed in claim 1, wherein said excited pseudo-property profile is accumulated for a fourth time period exceeding said first time period.

6. A method as claimed in claim 5, wherein accumulation of said excited pseudo-property profile employs weighting factors which are not all equal.

7. A method as claimed in claim 1, wherein said pseudo-property profile is a correlated difference profile which is calculated as the difference between a current measured said sheet property profile and a phase lagged said sheet property profile.

8. A method as claimed in claim 1, wherein said pseudo-property profile is a correlated variability profile which is calculated as a positive power of an absolute difference between a current measured said sheet property profile and a phase lagged said sheet property profile.

9. A method as claimed in claim 1, wherein a deduced property of said sheet manufacturing process is a mapping from actuators to a measured said profile.

10. A method as claimed in claim 1, wherein a deduced property of said sheet manufacturing process is a response shape of actuators in a measured profile.

11. A method as claimed in claim 1, wherein said sheet manufacturing process is a process for making paper, paperboard or tissue.

12. A method for identifying plural relations in a sheet manufacturing process, said method comprising the steps of:

a) specifying a first time period to be used as the cycle time of a cyclic excitation b) measuring sheet property profiles, c) collecting a first set of measured said sheet property profiles during a second time period which exceeds said first time period, d) calculating from said first set of sheet property profiles a reference pseudo-property profile using a phase lag substantially equal to half of said first time period, e) applying a cyclic excitation pulse to at least one actuator, with a cycle time substantially equal to said first time period, continuing for a third time period exceeding said first time period, f) measuring an excited sheet property profile g) collecting a second set of said measured said excited sheet property profiles for a fourth time period exceeding said first time period, h) calculating from said second set of sheet property profiles an excited pseudo-property profile using a phase lag substantially equal to half of said first time period, and i) deducing properties of said sheet manufacturing process from a difference between said excited pseudo-property profile and said reference pseudo-property profile.

13. A method as claimed in claim 12, wherein said fourth time period starts not sooner than one process dead-time after the start of the third time period, and ends not later than a sum of said process dead-time, first time period and measurement time for a single profile after an end of said third time period.

* * * * *

UNITED STATES PATENT AND TRADEMARK OFFICE
CERTIFICATE OF CORRECTION

PATENT NO. : 6,343,240 B1  
DATED : January 29, 2002  
INVENTOR(S) : John Shakespeare et al.

It is certified that error appears in the above-identified patent and that said Letters Patent is hereby corrected as shown below:

Title page,
Item [73], "Neles Paper Automation OY" should read -- Metso Paper Automation OY --.

Signed and Sealed this

Thirtieth Day of April, 2002

Attest:

JAMES E. ROGAN
*Attesting Officer*     *Director of the United States Patent and Trademark Office*